(12) United States Patent
Mahrouche et al.

(10) Patent No.: US 10,888,367 B2
(45) Date of Patent: Jan. 12, 2021

(54) CRYOABLATION METHOD AND SYSTEM

(71) Applicant: Medtronic CryoCath LP, Toronto (CA)

(72) Inventors: Rachid Mahrouche, LaSalle (CA); Dan Wittenberger, L'lle Bizard (CA)

(73) Assignee: Medtronic CryoCath LP

(*) Notice: Subject to any disclaimer, the term of this patent is extended or adjusted under 35 U.S.C. 154(b) by 436 days.

(21) Appl. No.: 15/922,510

(22) Filed: Mar. 15, 2018

(65) Prior Publication Data
US 2018/0199980 A1    Jul. 19, 2018

Related U.S. Application Data

(62) Division of application No. 14/329,571, filed on Jul. 11, 2014, now Pat. No. 9,956,024.

(51) Int. Cl.
*A61B 18/02* (2006.01)
*A61B 18/00* (2006.01)

(52) U.S. Cl.
CPC ..... *A61B 18/02* (2013.01); *A61B 2018/00011* (2013.01); *A61B 2018/00017* (2013.01); *A61B 2018/0022* (2013.01); *A61B 2018/00023* (2013.01); *A61B 2018/00041* (2013.01); *A61B 2018/00577* (2013.01); *A61B 2018/0212* (2013.01); *A61B 2018/0268* (2013.01)

(58) Field of Classification Search
CPC .......... A61B 18/02; A61B 2018/00011; A61B 2018/00017; A61B 2018/00023; A61B 2018/00041; A61B 2018/0022; A61B 2018/00577; A61B 2018/0212; A61B 2018/0268

USPC ..................................................... 606/20–26
See application file for complete search history.

(56) References Cited

U.S. PATENT DOCUMENTS 5,334,181 A    8/1994  Rubinsky et al.
5,545,015 A    8/1996  Scherrer
(Continued)

OTHER PUBLICATIONS

Baust, John G. et al. The molecular basis of cryosurgery, 2005 BJU International, 95, 1187-1191, doi:10.1111/i.1464-410X.2005.05502.x.

(Continued)

*Primary Examiner* — Michael F Peffley
*Assistant Examiner* — Khadijeh A Vahdat
(74) *Attorney, Agent, or Firm* — Christopher & Weisberg, P.A.

(57) ABSTRACT

A system and method for providing greater control over the temperature of a thermal treatment element of a medical device, enabling an operator to extend a thawing period of a cryoablation procedure. The system may include a fluid flow path that bypasses a subcooler, giving the operator selective control over the temperature of refrigerant delivered to the treatment element and, therefore, treatment element temperature. Additionally or alternatively, the system may include a fluid delivery conduit that is in communication with a liquid refrigerant and a gaseous refrigerant. Adjustment of the ratio of liquid to gaseous refrigerant also offers control over the treatment element temperature. Additionally or alternatively, the system may include one or more valves and/or heating elements in the fluid delivery and recovery conduits to control the treatment element temperature.

18 Claims, 8 Drawing Sheets

(56) References Cited

U.S. PATENT DOCUMENTS

| | | | |
|---|---|---|---|
| 6,635,053 | B1 | 10/2003 | Lalonde et al. |
| 7,780,657 | B2 | 8/2010 | Abboud et al. |
| 2002/0049438 | A1* | 4/2002 | Sharkey ............ A61B 18/1402 606/41 |
| 2003/0171742 | A1* | 9/2003 | Mihalik ............ A61M 25/0029 606/22 |
| 2003/0220634 | A1 | 11/2003 | Ryba et al. |
| 2006/0178662 | A1 | 8/2006 | Ripley et al. |
| 2009/0036823 | A1* | 2/2009 | LePivert ............ A61B 18/02 604/21 |
| 2009/0088735 | A1* | 4/2009 | Abboud .......... A61M 25/10182 606/22 |
| 2009/0171333 | A1 | 7/2009 | Hon |
| 2009/0182319 | A1 | 7/2009 | Lane et al. |
| 2011/0306958 | A1 | 12/2011 | Berzak et al. |
| 2013/0204241 | A1* | 8/2013 | Baust ................ A61B 18/082 606/24 |

OTHER PUBLICATIONS

Whittaker, D. K., PhD FDS RCS, Mechanisms of tissue destruction following cryosurgery, Annals of the Royal College of Surgeons of England (1984) vol. 66.

Gage, Andrew A. et al., Effect of Varying Freezing and Thawing Rates in Experimental Cryosurgery, Cryobiology 22, 175-182 (1985).

Mazur, Peter, Freezing of living cells: mechanisms and implications, Am. J. Physiol. 247 (Cell Physiol. 16): C125-C142, 1984.

Theodorescu, Dan MD, PhD., Cancer Cryotherapy: Evolution and Biology, Reviews in Urology, vol. 6, Suppl. 4 2004.

International Search Report and Written Opinion dated Aug. 28, 2015, for corresponding International Application No. PCT/CA2015/000380; International Filing Date: Jun. 15, 2015 consisting of 11 pages.

Supplementary European Search Report for Application No. EP 15818849 dated Feb. 8, 2018.

* cited by examiner

CRYOABLATION METHOD AND SYSTEM

CROSS-REFERENCE TO RELATED APPLICATION

This application is a divisional of and claims priority to patent application Ser. No. 14/329,571, filed Jul. 11, 2014, now U.S. Pat. No. 9,956,024, entitled CRYOABLATION METHOD AND SYSTEM, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for providing greater control over the temperature of a thermal treatment element of a medical device, enabling an operator to extend a thawing period of a cryoablation procedure.

BACKGROUND OF THE INVENTION

Methods of thermally treating tissue are frequently used for a wide variety of medical purposes. For example, cryoablation, by which tissue may be destroyed, may be used to treat cardiac arrhythmia, to ablate tumors in the treatment of cancer, and for dermatological and obstetric procedures. Further, cooling tissue to sub-lethal temperatures is commonly used in electrophysiology studies.

Regardless of the tissue being treated, the permanency of the lesion created by a cryoablation procedure is of the utmost importance. The target tissue must be completely and permanently affected, which prevents the recurrence of the condition being treated. In the treatment of certain forms of arrhythmia, including atrial fibrillation (AF), permanent electrical conduction blocks must be created at specific locations in the heart. Therefore, continuous, transmural lesions must be created, ensuring that all myocardial cells in the target tissue are destroyed. Specifically, myocytes are killed acutely by cold-induced injury through several mechanisms that can include cell membrane rupture due to ice formation, osmotic imbalance, dehydration, damage to the mitochondria, and delayed apoptotic processes.

The type and severity of the damage to tissue cells is influenced by several parameters of the treatment process. In a cryoablation procedure, for example, these parameters may include duration of the freeze, treatment temperature, cooling and thawing rate, and the number of freeze-thaw-freeze cycles. In fact, extending the thawing phase of a cryoablation procedure by creating a temperature plateau at a mildly cold temperature, between approximately −20° C. and approximately −25° C., may result in more complete cell destruction and, therefore, a reduced likelihood of reconduction. Additionally, maintaining the treatment element in this temperature range may reduce the occurrence of collateral damage by preventing the freeze zone from penetrating too deeply within the tissue.

Current cardiac cryoablation systems operate at a controlled refrigerant flow to the treatment device, resulting in an operating temperature that is the lowest achievable in the given conditions. That is, the operator does not have the means to control the minimum temperature or the cooling and thawing rates. The only parameters that can be controlled are the duration of the freeze and the number of freeze-thaw-freeze cycles.

It is therefore desirable to provide a method and system by which parameters of a cryoablation procedure may be fully controllable. For example, it is desirable to provide a method and system by which duration of the freeze, treatment temperature, cooling and thawing rates, and the number of freeze-thaw-freeze cycles may be controlled by the operator.

SUMMARY OF THE INVENTION

The present invention advantageously provides a method and system for providing greater control over the temperature of a thermal treatment element of a medical device, enabling an operator to extend a thawing period of a cryoablation procedure. In one embodiment, a system for controllable adjustment of the temperature of a treatment element of a medical device may include a fluid delivery conduit including an upstream portion and a downstream portion, a subcooler located between the upstream fluid flow path and the downstream fluid flow path, a bypass fluid flow path having a first end that is in direct communication with the upstream fluid flow path and a second end that is in direct communication with the downstream fluid flow path, a first valve located in the upstream fluid flow path between the subcooler and the first end of the bypass fluid flow path, and a second valve located in the bypass fluid flow path. The system may further include a refrigerant source in fluid communication with the fluid delivery conduit. As an example, the treatment element may reach a minimum treatment temperature when the first valve is completely open and the second valve is completely closed, and may reach a maximum treatment temperature when the first valve is completely closed and the second valve is completely open. The refrigerant source may be a liquid refrigerant source, and the system may further include a gaseous refrigerant source in fluid communication with the fluid delivery conduit. Adjusting the ratio of gaseous refrigerant to liquid refrigerant may selectively control the temperature of the treatment element. The liquid refrigerant source may be a first tank and the gaseous refrigerant source may be a second tank. Alternatively, the liquid refrigerant source and the gaseous refrigerant source may be a common tank (that is, both liquid refrigerant source and gaseous refrigerant source may be located in the same tank). The common tank may define a fluid reservoir, the liquid refrigerant source being at the bottom of the fluid reservoir and the gaseous refrigerant source being at the top of the fluid reservoir. Further, the common tank may include a first valve in fluid communication with the liquid refrigerant source and a second valve in fluid communication with the gaseous refrigerant source, manipulation of at least one of the first and second valves adjusting the ratio of gaseous refrigerant to liquid refrigerant. For example, at least one of the first and second valves may be manipulated until the treatment element achieves a temperature of between approximately −20° C. and approximately −25° C. The tank may further include a dip tube in communication with the first valve and extending into the liquid refrigerant source. The first and second valves may be on the same end of the common tank, or they may be on opposite ends of the common tank. The fluid delivery conduit may be in fluid communication with the treatment element, and the system may further include a fluid recovery conduit in fluid communication with the treatment element, a first valve in the fluid recovery conduit, and a second valve in the fluid delivery conduit, independent manipulation of at least one of the first and second valves selectively controlling the temperature of the treatment element. Alternatively, the system may include only a valve in the fluid recovery conduit, manipulation of the valve selectively controlling the temperature of the treatment element.

A system for adjusting a treatment temperature of a cryoablation device may include a refrigerant source, a fluid delivery conduit configured to be in fluid communication with the refrigerant source and the cryoablation device, a fluid recovery conduit configured to be in fluid communication with the cryoablation device, and a heating element in thermal exchange with the fluid delivery conduit. The heating element may be a thermoelectric heater. Additionally or alternatively, the fluid recovery conduit may include a heating fluid flow path, at least a portion of the heating fluid flow path being in thermal exchange with the fluid delivery conduit. The heating fluid flow path may include a valve, manipulation of the valve selectively affecting the temperature of at least a portion of the cryoablation device.

A system for adjusting a treatment temperature of a treatment element of a cryoablation device may include: a fluid delivery conduit including an upstream portion and a downstream portion, the upstream portion being in fluid communication with a refrigerant reservoir and the downstream portion being in fluid communication with the treatment element; a subcooler located between the upstream fluid flow path and the downstream fluid flow path; a bypass fluid flow path having a first end that is in direct communication with the upstream fluid flow path and a second end that is in direct communication with the downstream fluid flow path; a first valve located in the upstream fluid flow path between the subcooler and the first end of the bypass fluid flow path; and a second valve located in the bypass fluid flow path, the refrigerant reservoir containing both a refrigerant in a gaseous state and a refrigerant in a liquid state, the refrigerant reservoir having a third valve for delivering the gaseous state refrigerant to the fluid delivery conduit and a fourth valve for delivering the liquid state refrigerant to the fluid delivery conduit, independent manipulation of at least one of the first, second, third, and fourth valves controlling the temperature of the treatment element. At least one of the first, second, third, and fourth valves may be manipulated so that the treatment element achieves a temperature of between approximately −20° C. and approximately −25° C.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
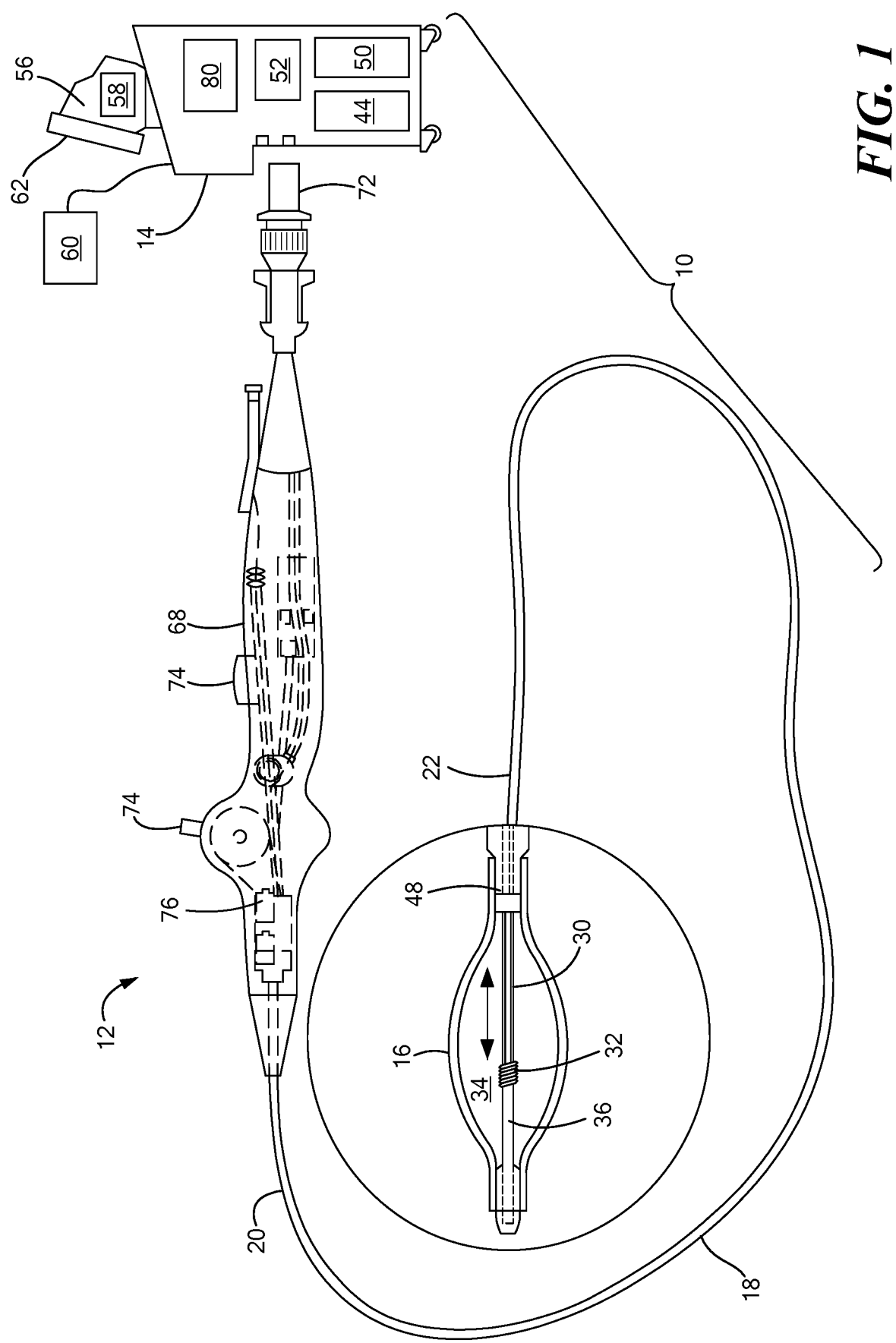
FIG. 1 shows an exemplary cryoablation system including a treatment device having a treatment element.

The present invention advantageously provides a method and system by which parameters of a cryoablation procedure may be fully controllable. For example, the duration of the freeze, treatment temperature, cooling and thawing rates, and the number of freeze-thaw-freeze cycles may be fully controllable by the operator. Referring now to the drawing figures in which like reference designations refer to like elements, an exemplary embodiment of a cryoablation system including a treatment device having a treatment element in accordance with principles of the present invention is shown in FIG. 1 and generally designated as "10." The system 10 may generally include a treatment device 12, which may be referred to herein as a catheter, that may be coupled to a control unit or operating console 14. The catheter 12 may be configured to interact with tissue, such as with a treatment element 16. Further, the catheter 12 may include one or more electrodes with mapping and/or ablation functionality (not shown).

The catheter 12 may include an elongate body 18 passable through a patient's vasculature and/or proximate to a tissue region for diagnosis or treatment. The elongate body 18 may define a proximal portion 20 and a distal portion 22, and may further include one or more lumens disposed within the elongate body 18 thereby providing mechanical, electrical, and/or fluid communication between the proximal portion of the elongate body 18 and the distal portion of the elongate body 18. For example, the medical device 12 may further include a fluid delivery conduit 30 traversing at least a portion of the elongate body 18 and towards the distal portion 22. The delivery conduit 30 may be coupled to or otherwise extend from the distal portion 22 of the elongate body 18 into the treatment element 16. Although the treatment element 16 is shown in FIG. 1 as a balloon, it will be understood that the treatment element 16 may be any treatment element through which refrigerant may flow and that is capable of thermally affecting tissue.

One or more fluid injection elements 32 in fluid communication with the fluid delivery conduit 30 may be disposed within the interior chamber 34 of the balloon 16. The fluid injection element 32 may be of any configuration suitable for delivering refrigerant or other fluid from the fluid delivery conduit 30 into the balloon 16. As a non-limiting example, a fluid injection element 32 may include a plurality of windings about a shaft or actuation element 36 within the chamber 34 (as shown in FIG. 1). Further, the fluid injection element 32 may include one or more openings or ports therein to provide for the delivery and, optionally, directed ejection of fluid from the fluid delivery conduit 30 to the chamber 34 of the balloon 16.

The system 10 may also include one or more fluid supply reservoirs 44, such as pressurized tanks, that include a coolant, cryogenic refrigerant, or the like in fluid communication with the fluid delivery conduit 30 and fluid injection element 32. As a non-limiting example, a fluid supply reservoir 44 may be a refrigerant tank as shown and described in more detail below. The system 10 may also include an exhaust or scavenging system for recovering or venting expended refrigerant for re-use or disposal. The scavenging system may include a fluid recovery conduit 48 defining a passage for the recovery of expanded refrigerant, a fluid recovery reservoir 50, and a vacuum pump 52 for creating a pressure gradient to draw expanded refrigerant from the balloon chamber 34 into the fluid recovery conduit 48 and then into the fluid recovery reservoir 50 (that is, from the distal portion of the device to the proximal portion of the device and into the operating console). The system's fluid flow path may include at least the fluid delivery conduit 30 and the fluid recovery conduit 48, in addition to various other conduits and/or secondary flow paths. Further, although the fluid supply reservoir 44 and the fluid recovery reservoir 50 each may each located within or external to operating console 14, they are referred to as being part of the operating console 14 for simplicity. The operating console 14 may also include pumps, valves, controllers or the like to recover and/or re-circulate fluid delivered to the handle, the elongate body, and/or the fluid pathways of the catheter 12, as described in more detail below.

The operating console 14 may include one or more controllers, processors, and/or software modules containing instructions or algorithms to provide for the automated operation and performance of the features, sequences, or procedures described herein. For example, the operating console 14 may include one or more computers 56 that include one or more processors 58 for receiving signals from one or more sensors throughout the system 10, and or for the automatic, semi-automatic, and/or manual operation of the system 10. The one or more computers 56 may include one or more user input devices 60 by which a user can program system parameters such as the inflation and deflation of the balloon 16, circulation of refrigerant through the fluid delivery and recovery conduits, and/or the operation of one or more electrodes or other thermal delivery elements. The user input devices 60 may include keyboards, knobs, buttons, dials, foot pedals, mice, touchscreens, voice input units, and/or switches. Additionally, the user may use the user input devices to override the automatic operation of the system 10 either programmed into or predetermined by the operating console 14. Still further, signals received by the one or more processors 58 may be used to automatically or semi-automatically control the configuration of the balloon 16 (for example, by extending or retracting the actuation element 36). The one or more computers 56 may further includes one or more displays 62, such as computer screens or other visual elements in communication with the one or more processors 58 and/or user input devices 60. Finally, the operating console 14 may include one or more speakers or other audio alert generators that are in communication with the one or more processors 58 and/or the user input devices 60.

The catheter 12 may include a handle 68 coupled to the proximal portion 20 of the elongate body 18. The handle 68 can include circuitry for identification and/or use in controlling of the catheter 12 or another component of the system 10. For example, the handle 68 may include one or more sensors to monitor system parameters such as the fluid pressure within the catheter 12 or one or more fluid flow paths of the system. Additionally, the handle 68 may also include connectors 72 that are matable directly to a fluid supply/exhaust and operating console 14 or indirectly by way of one or more umbilicals. The handle 68 may further include blood detection circuitry in fluid and/or optical communication with the injection, exhaust and/or interstitial lumens. The handle 68 may also include a pressure relief valve in fluid communication with the fluid delivery conduit 30 and/or exhaust lumen to automatically open under a predetermined threshold value in the event that value is exceeded.

The handle 68 may also include one or more actuation or control features that allow a user to control, deflect, steer, or otherwise manipulate a distal portion of the medical device from the proximal portion of the medical device. For example, the handle 68 may include one or more components such as a lever or knob 74 for manipulating the elongate body 18, shaft 36, a guidewire, and/or additional components of the catheter 12.

The system 10 may further include one or more sensors 76 to monitor the operating parameters throughout the system 10, including for example, pressure, temperature, flow rates, volume, or the like in the operating console 14 and/or the catheter 12, in addition to monitoring, recording or otherwise conveying measurements or conditions within the catheter 12 or the ambient environment at the distal portion of the catheter 12. The sensor(s) 76 may be in communication with the operating console 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the catheter 12 and system 10. Such valves, controllers, or the like may be located in a portion of the medical device 12 and/or in the operating console 14.

While the medical device 12 may be in fluid communication with a fluid source to cryogenically treat selected tissue, it is also contemplated that the medical device 12 may additionally include one or more electrically conductive portions or electrodes thereon coupled to a radiofrequency generator or power source 80 as a treatment or diagnostic mechanism. If the catheter 12 includes thermoelectric cooling elements or electrodes capable of transmitting radiofrequency (RF), ultrasound, microwave, electroporation energy, or the like, the elongate body 18 may include a lumen in electrical communication with a power source 80.

Referring now to FIGS. 2-5, schematic diagrams of a system providing fully controllable cryoablation parameters are shown. As discussed above, the system fluid flow path may include one or more valves, conduits, secondary flow paths, one or more fluid supply reservoirs 44, one or more fluid recovery reservoirs 50, a vacuum pump 52, and other system components. The system 10 may also include one or more subcoolers 82 with various refrigeration components such as a compressor, condenser, capillary tube, thermoelectric elements, and/or heat exchanger. Currently known cryoablation systems frequently include subcoolers to ensure that the refrigerant is delivered to the balloon in a fully liquid state, because the refrigerant has maximum refrigeration potential (maximum enthalpy). For example, a liquid refrigerant delivered to the balloon 16 may cause the balloon 16 to reach a temperature of approximately −80° C. However, a system that always delivers liquid refrigerant to the balloon at maximum refrigeration potential does not offer a means to control or adjust the temperature of the balloon and, therefore, to extend the thawing phase by creating a temperature plateau in the range of between approximately −20° C. and approximately −25° C. (referred to herein as the "plateau temperature"). The thawing period may be maintained for between approximately 2 seconds to approximately 40 seconds. For example, the thawing period may be maintained for approximately 20 seconds to achieve the desired result.

Figure 2:
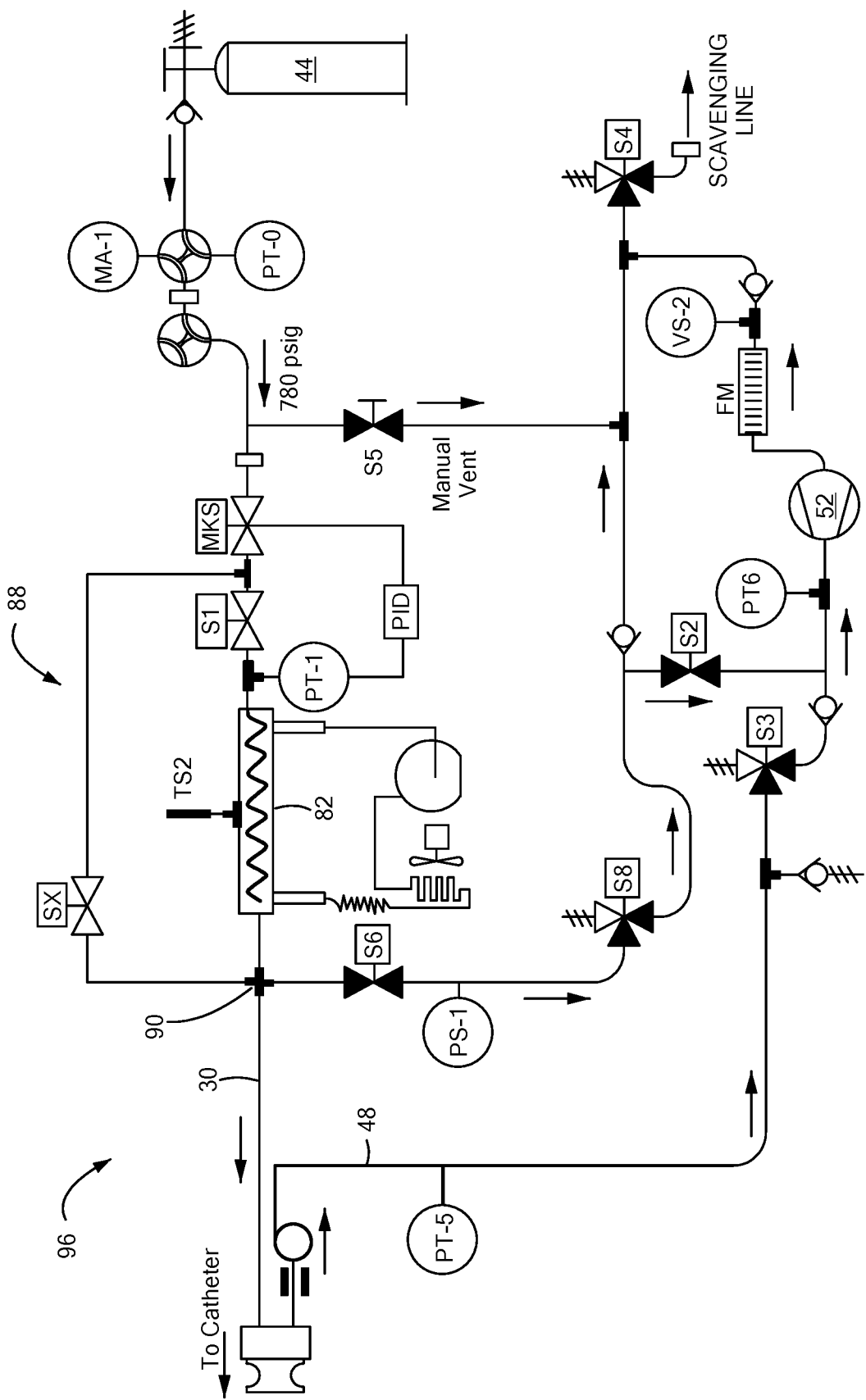
FIG. 2 shows a first schematic diagram of a system providing fully controllable cryoablation parameters.

One means for providing a controllable balloon temperature is shown in FIG. 2. The system 10 shown in FIG. 2 may include a heat exchanger bypass flow path 88 that allows coolant to be delivered to the balloon 16 while completely or partially avoiding the subcooler 82. The system 10 may include a solenoid valve S1 that is upstream of the subcooler 82 (that is, between the subcooler 82 and the refrigerant supply reservoir 44) and a bypass flow path 88, the bypass flow path 88 having a first end that is located upstream of valve S1, a second end that is located downstream of the subcooler 82, and a solenoid valve SX located between the first end and the second end. For example, directing refrigerant through the bypass flow path 88 may avoid the subcooler 82 altogether. Valves S1 and/or SX may be opened or closed to modify the temperature of the balloon 16. Current cryoablation systems may be retrofitted with a bypass flow path 88 (which may include, for example, a conduit and one or more valves) to add temperature adjustment functionality to existing systems. Refrigerant that passes through a subcooler may exist at a temperature below its normal saturation temperature or boiling point. Thus, the refrigerant may be in a fully liquid state upon exiting the subcooler. If valve SX is closed and valve S1 is open, the refrigerant will pass from the fluid supply reservoir 44 and through the subcooler 82. Liquid refrigerant may then pass from the subcooler into the balloon chamber 34 via the fluid delivery conduit 30, the refrigerant being in a fully liquid state. As the refrigerant exits the higher-pressure environment of the fluid delivery conduit 30 and fluid injection element 32 and into the lower-pressure balloon chamber 34, the refrigerant will expand into a gas (or, if delivered in a gaseous state, the refrigerant will simply expand and remain in the gaseous state) and the temperature of the refrigerant will decrease by the Joule-Thomson effect. This decrease in temperature within the chamber 34 allows the balloon 16 to remove heat from surrounding tissue, which may result in cryoablation of the tissue.

If, on the other hand, a warmer refrigerant (and, therefore, balloon 16) temperature is desired, operation of the subcooler 82 may be duty cycled so that when the subcooler 82 is "on" (that is, for example, heat exchange is allowed to occur within the subcooler 82, such as by activating a thermoelectric device or allowing heat exchange between the refrigerant and a secondary cooled liquid) the refrigerant enters the balloon 16 in a liquid state. Conversely, when the subcooler 82 is "off" (that is, for example, heat exchange does not occur within the subcooler 82, such as by deactivating a thermoelectric device or preventing heat exchange between the refrigerant and a secondary cooled liquid), at least a portion of the refrigerant may be delivered to the balloon 16 in a gaseous state. So, some portion of the refrigerant may be in a liquid state and some portion of the refrigerant may be in a gaseous state, with the gaseous refrigerant causing the balloon 16 to reach temperatures greater than it would if the refrigerant were delivered in a fully liquid state. This is because the gaseous portion of the refrigerant does not expand to create a lower temperature within the chamber 34.

Although duty cycling the subcooler 82 may be effective in producing a warmer balloon temperature, the temperature-modifying effects may not be instantaneous because adjusting subcooler parameters may produce a delayed effect on the temperature of the refrigerant passing therethrough. When immediate or substantially immediate temperature adjustment is desired, solenoid valve S1 may be closed while solenoid valve SX may be open, causing the refrigerant to flow through the subcooler bypass flow path 88. Bypassing the subcooler 82 may mean that the refrigerant does not become fully liquefied and at least a portion of the refrigerant remains in the gaseous state.

Figure 3:
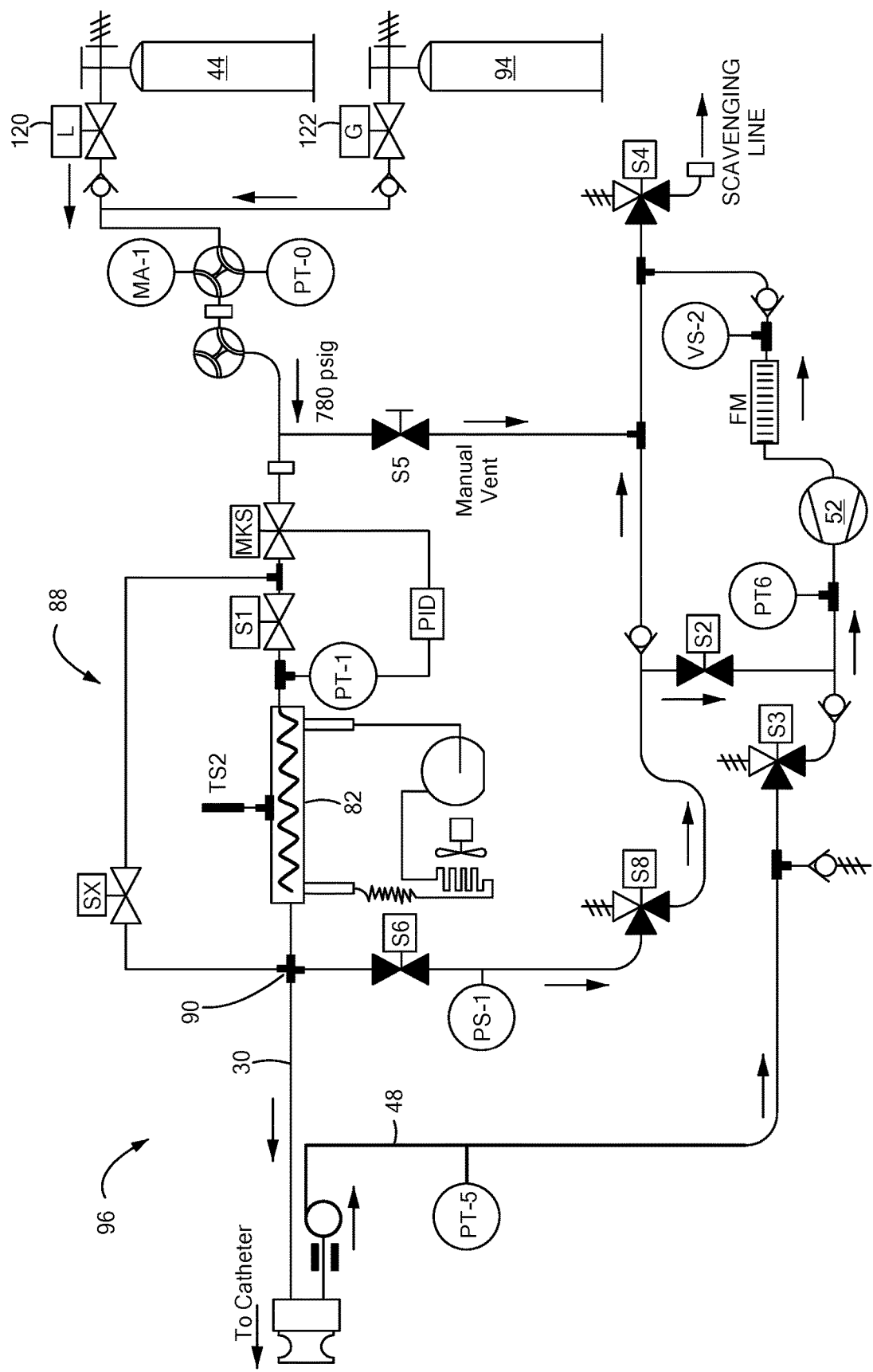
FIG. 3 shows a second schematic diagram of a system providing fully controllable cryoablation parameters.
Figure 4:
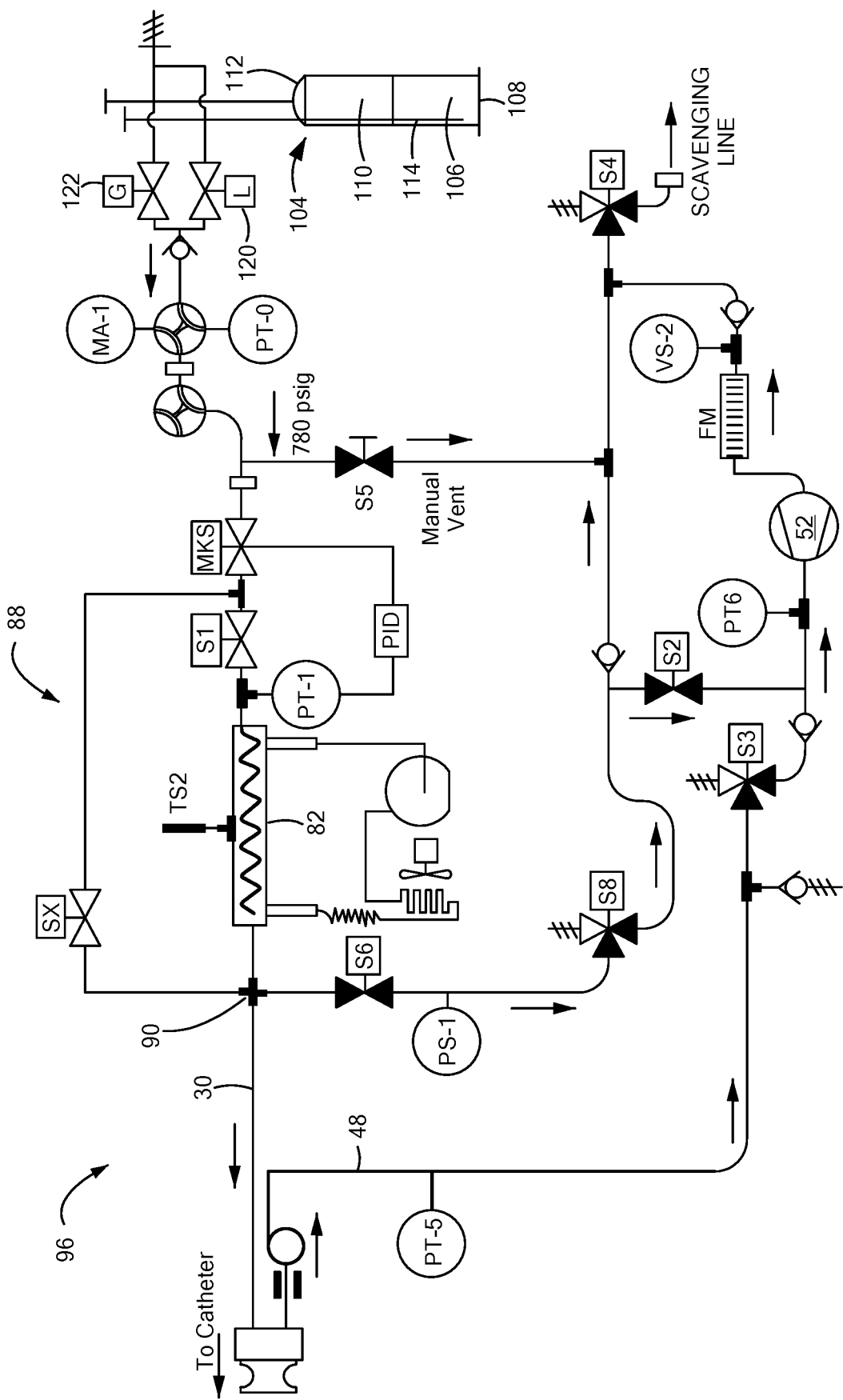
FIG. 4 shows a third schematic diagram of a system providing fully controllable cryoablation parameters.
Figure 5:
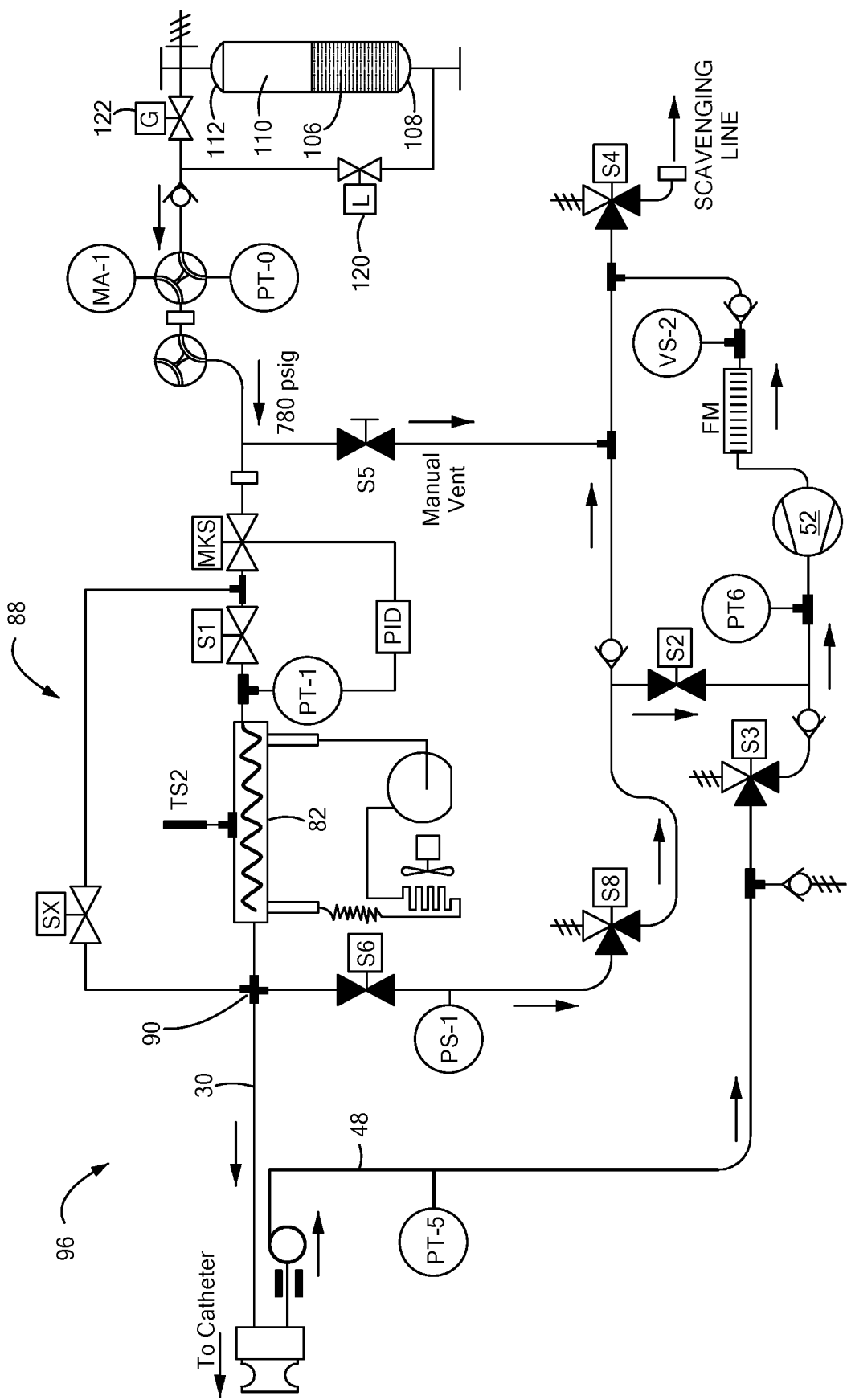
FIG. 5 shows a fourth schematic diagram of a system providing fully controllable cryoablation parameters.

Another means for providing a controllable balloon temperature is shown in FIGS. 3-5. Like the system 10 in FIG. 2, the system 10 in FIGS. 3-5 may also include a subcooler bypass flow path 88. Thus, these systems may be operated similarly to the system of FIG. 2. However, unlike systems that include a fluid supply of liquid refrigerant only, the systems in FIGS. 3-5 may include a source of liquid refrigerant and a source of gaseous refrigerant. For example, each refrigerant source may be an individual tank. Thus, the temperature of the balloon 16 may be adjusted by the delivery of a mixture of liquid and gaseous refrigerant, the mixture being controlled at the refrigerant source instead of by adjusting, for example, subcooler operation. However, it will be understood that a controlled mixture of gaseous and liquid refrigerant may also be delivered to the subcooler 82 in cases where the subcooler includes a secondary refrigerant in thermal exchange with the refrigerant being delivered to the balloon 16. That is, the cooling effect of the subcooler on the refrigerant being delivered to the balloon 16 may be determined by the temperature of the secondary coolant within, which, in turn, may be determined by the ratio of gaseous to liquid refrigerant. It further will be understood that the balloon 16 temperature may be adjusted both by the method shown and described in FIG. 2 and by the method shown and described in FIGS. 3-5. As shown in FIG. 3, the system 10 may include a liquid refrigerant supply reservoir 44 and a separate gaseous refrigerant supply reservoir 94, both of which being in fluid communication with the system flow path 96 and the balloon chamber 34. The gaseous refrigerant supply reservoir 94 may also be added to existing systems. The delivery rate of the liquid refrigerant from the liquid refrigerant supply reservoir 44 may be controlled via valve 120, and the delivery rate of the gaseous refrigerant from the gaseous refrigerant supply reservoir 94 may be controlled via valve 122. Thus, the mixture or ratio of gaseous to liquid refrigerant may be controlled by the independent and selective manipulation of valve 120 and/or valve 122.

Alternatively, as shown in FIG. 4, the fluid refrigerant supply and the gaseous refrigerant supply may be housed in a common reservoir or tank 104. The common reservoir 104 may include liquid refrigerant 106 at the bottom 108 of the reservoir 104 and gaseous refrigerant 110 at the top 112 of the reservoir 104, as the denser liquid may settle to the bottom of the reservoir 104. As used herein, the term "bottom" may refer to any portion of the reservoir 104 to which gravity causes the liquid refrigerant 106 to settle. As used herein, the term "top" may refer to the portion of the reservoir 104 that is vertically aligned with and opposite to the bottom. The reservoir 104 may include a dip stick 114 in communication with a first valve 120 for drawing and delivering liquid refrigerant 106 from the bottom 108 of the reservoir 104 and into the balloon 16. The reservoir 104 may further include a second valve 122 for drawing and delivering gaseous refrigerant 110 from the top 112 of the reservoir 104. Thus, the first 120 and second 122 valves may both be located on the same end of the reservoir 104. The mixture of the liquid 106 and gaseous 110 refrigerants delivered to the balloon 16 may be adjusted by independently and selectively adjusting valves 120 and 122 between a closed position and a fully open position.

Alternatively, as shown in FIG. 5, the common reservoir 104 may include a first valve 120 at the bottom 108 of the reservoir 104 for adjusting the flow of liquid refrigerant 106 and a second valve 122 at the top 112 of the reservoir 104 for adjusting the flow of gaseous refrigerant 110. The liquid refrigerant 106 may be at the bottom 108 of the reservoir 104 and the gaseous refrigerant 110 may be at the top 112, as shown and described in FIG. 4, and therefore the liquid refrigerant 106 may be drawn from the first valve 120 at the bottom 108 whereas the gaseous refrigerant 110 may be drawn from the second valve 122 at the top 112. Like the system of FIG. 4, the mixture of the liquid 106 and gaseous 110 refrigerant delivered to the balloon 16 may be adjusted by independently and selectively adjusting valves 120 and 122 between a closed position and a fully open position. The common reservoir 104 as shown in either FIG. 4 or FIG. 5 may be added to existing systems.

Figure 6A:
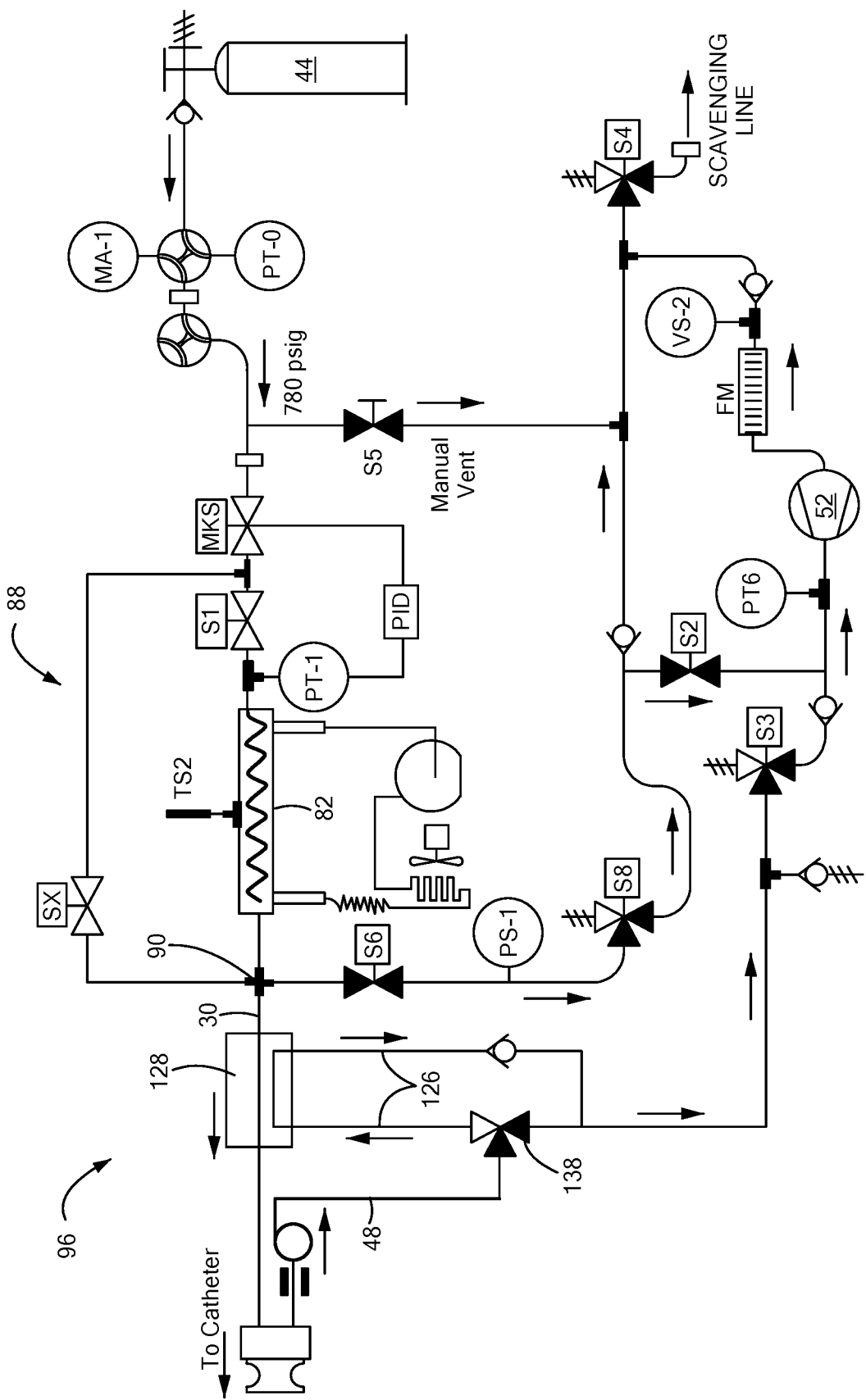
FIG. 6A shows a fifth schematic diagram of a system providing fully controllable cryoablation parameters.
Figure 6B:
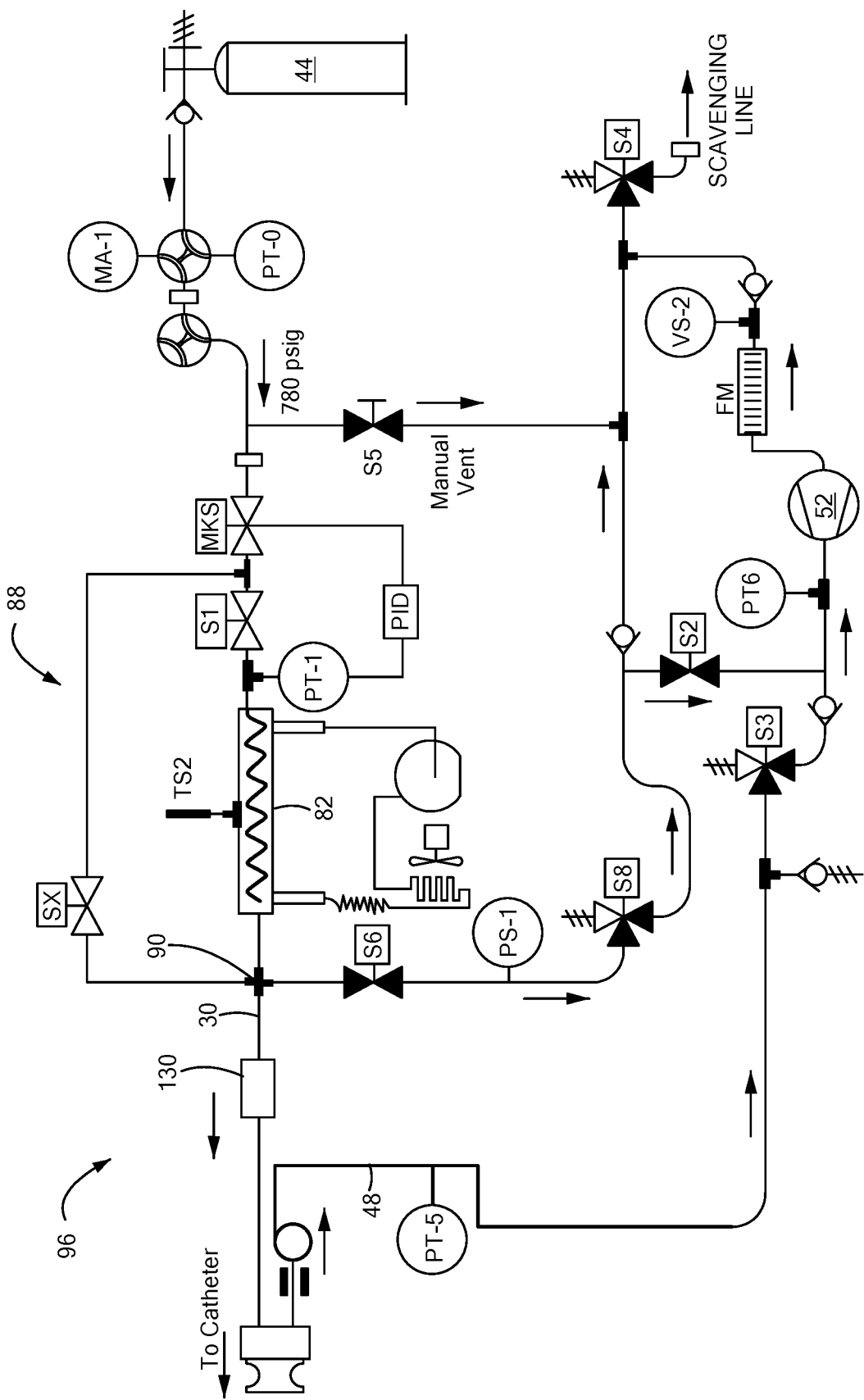
FIG. 6B shows a sixth schematic diagram of a system providing fully controllable cryoablation parameters.

Another means for providing a controllable balloon temperature is shown in FIGS. 6A and 6B. The system in FIGS. 6A and 6B may include one or more heating mechanisms. For example, the heating mechanism may include a heat exchange flow path 126 that includes an area 128 at which the delivery conduit 30 and the recovery conduit 48 may be in thermal exchange with one another (as shown in FIG. 6A). Solenoid valve 138 may be selectively opened or closed to allow warmer fluid in the recovery conduit 48 to be in thermal exchange with the refrigerant in the delivery conduit 30 via heat exchange flow path 126. As a result, the temperature of the refrigerant in the delivery conduit 30 may be increased.

Additionally or alternatively, the system 10 may include one or more thermoelectric heating elements 130 distributed at any point(s) in the system flow path 96 between the operating console 14 and the catheter 12 on the fluid delivery side (as shown in FIG. 6B). Generally, thermoelectric heating elements 130 would not be located within the catheter 12 in order to avoid the need to send additional power into the catheter 12.

Figure 7:
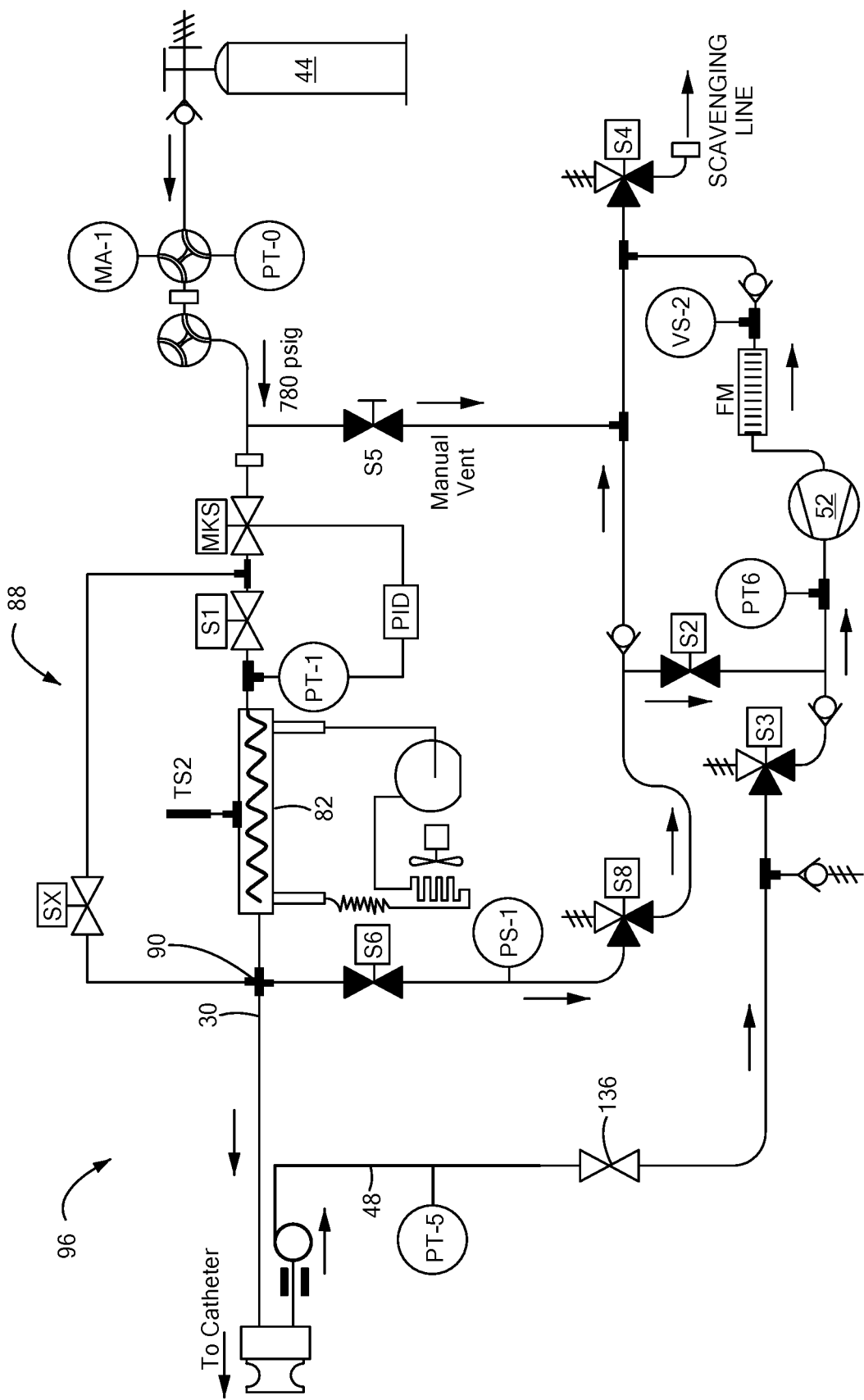
FIG. 7 shows a seventh schematic diagram of a system providing fully controllable cryoablation parameters.

Another means for providing a controllable balloon temperature is shown in FIG. 7. Like the systems shown and described in FIGS. 2-6, the system 10 of FIG. 7 may also include a subcooler bypass flow path 88. The system 10 in FIG. 7 may also include a proportional valve 136 in the fluid recovery conduit 48 that may be adjusted to create a restriction in the fluid recovery conduit 48. This restriction may slow refrigerant flow rate from the balloon chamber 34 into the fluid recovery conduit 48, thereby increasing the pressure within the balloon chamber 34. The pressure increase within the chamber 34 may cause an increase in the boiling point of the refrigerant therein. As a result, the refrigerant within the chamber 34, and thus the balloon 16, may have a warmer temperature than if the refrigerant were allowed to freely flow from the chamber 34 into the fluid recovery conduit 48. Adjusting the valve 136 between the closed position and the fully open position may therefore allow the operator to control the temperature of the balloon 16. For example, the balloon temperature may be lower when the valve 136 is fully open than when the valve 136 is fully or substantially closed.

Similarly, proportional valve MKS in the fluid delivery conduit 30 and valve 136 in the fluid recovery conduit 48 may be individually and selectively controlled, either sequentially or simultaneously, to adjust the temperature of the balloon 16. For example, fully or substantially closing valve 136 and/or fully or substantially closing valve 136 may produce a warmer balloon temperature than fully opening both valves 136 and 138. Pressure transducer PT5 may monitor the fluid recovery conduit 48 pressure and transmit data to the operating console 14.

For any of the above embodiments, one or more temperature and/or pressure sensors 76 located in the balloon chamber 34 or any other point within the system flow path 96 may transmit data to the operating console 14, which information may be processed and displayed or otherwise communicated to the operator. Based on the transmitted and/or communicated data, one or more system parameters may be adjusted automatically or semi-automatically by the one or more processors, or manually by the operator. The one or more processors 58 may be programmed to execute one or more algorithms to communicate system parameters to the operator and/or suggest automatic control tasks to the operator, and/or automatically or semi-automatically control system parameters (for example, open or close one or more valves, adjust the ratio of liquid to gaseous refrigerant, and the like) to adjust the temperature of the balloon 16 and, therefore, the effect the catheter 12 has on target tissue. For example, if one or more temperature sensors, mapping electrodes, timers, or the like indicates to the one or more processors 58 that the target tissue has been ablated, or the treatment has gone on for a predetermined amount of time, the one or more processors 58 may automatically control one or more valves (such as to adjust the liquid to gaseous refrigerant, bypass the subcooler, and/or restrict the fluid recovery conduit 48) to increase the temperature of the balloon 16 to a temperature within a range of between approximately −20° C. and approximately −25° C. in order to extend the thawing phase of the treatment, which may result in more complete cell destruction and therefore in a reduced likelihood of reconduction.

Any of the system components shown and described herein may be used alone or in combination with any of the other system components shown and described herein in order to achieve a desired result. Further, the system components may be added to existing cryoablation systems to provide a fully controllable balloon temperature.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for controllable adjustment of a temperature of a treatment element of a medical device, the system comprising:
   a fluid delivery conduit including an upstream portion and a downstream portion;
   a subcooler located between the upstream portion and the downstream portion;
   a bypass fluid flow path having a first end that is in direct communication with the upstream portion and a second end that is in direct communication with the downstream portion;
   a first valve located in the upstream portion between the subcooler and the first end of the bypass fluid flow path;
   a second valve located in the bypass fluid flow path;
   a liquid refrigerant source in fluid communication with the fluid delivery conduit; and
   a gaseous refrigerant source in fluid communication with the fluid delivery conduit, the liquid refrigerant source and the gaseous refrigerant source are a common tank, the common tank including a first valve in fluid communication with the liquid refrigerant source and a second valve in fluid communication with the gaseous refrigerant source, manipulation of at least one of the first and second valves is configured to adjust a ratio of gaseous refrigerant to liquid refrigerant.

2. The system of claim 1, wherein the treatment element reaches a minimum treatment temperature when the first valve is completely open and the second valve is completely closed.

3. The system of claim 1, wherein the treatment element reaches a maximum treatment temperature when the first valve is completely closed and the second valve is completely open.

4. The system of claim 1, wherein adjusting a ratio of gaseous refrigerant to liquid refrigerant selectively controls the temperature of the treatment element.

5. The system of claim 1, wherein the common tank defines a fluid reservoir, the liquid refrigerant source being at a bottom of the fluid reservoir and the gaseous refrigerant source being at a top of the fluid reservoir.

6. The system of claim 1, wherein the common tank further includes a dip stick in communication with the common tank first valve and extending into the liquid refrigerant source.

7. The system of claim 1, wherein the common tank first and second valves are on a same end of the common tank.

8. The system of claim 1, wherein the common tank first and second valves are on opposite ends of the common tank.

9. A system for adjusting a treatment temperature of a cryoablation device, the system comprising:
a liquid refrigerant source;
a fluid delivery conduit configured to be in fluid communication with the liquid refrigerant source and the cryoablation device;
a gaseous refrigerant source in fluid communication with the fluid delivery conduit, the liquid refrigerant source and the gaseous refrigerant source are a common tank, the common tank including a first valve in fluid communication with the liquid refrigerant source and a second valve in fluid communication with the gaseous refrigerant source, manipulation of at least one of the first and second valves is configured to adjust a ratio of gaseous refrigerant to liquid refrigerant;
a fluid recovery conduit configured to be in fluid communication with the cryoablation device; and
a heating element in thermal exchange with the fluid delivery conduit.

10. The system of claim 9, wherein the heating element is a thermoelectric heater.

11. The system of claim 9, wherein the fluid recovery conduit includes a heating fluid flow path, at least a portion of the heating fluid flow path being in thermal exchange with the fluid delivery conduit.

12. The system of claim 11, wherein the heating fluid flow path includes a third valve, manipulation of the third valve selectively affecting a temperature of at least a portion of the cryoablation device.

13. A system for adjusting a treatment temperature of a treatment element of a cryoablation device, the system comprising:
a fluid delivery conduit including an upstream portion and a downstream portion, the upstream portion being in fluid communication with a refrigerant reservoir and the downstream portion being in fluid communication with the treatment element;
a subcooler located between the upstream portion and the downstream portion;
a bypass fluid flow path having a first end that is in direct communication with the upstream portion and a second end that is in direct communication with the downstream portion;
a first valve located in the upstream portion between the subcooler and the first end of the bypass fluid flow path; and
a second valve located in the bypass fluid flow path,
the refrigerant reservoir containing both a refrigerant in a gaseous state and a refrigerant in a liquid state, the refrigerant reservoir having a third valve for delivering the refrigerant in the gaseous state to the fluid delivery conduit and a fourth valve for delivering the refrigerant in the liquid state to the fluid delivery conduit.

14. The system of claim 13, wherein independent manipulation of at least one of the first, second, third, and fourth valves controls the treatment temperature of the treatment element.

15. The system of claim 14, wherein at least one of the first, second, third, and fourth valves are manipulated so that the treatment element achieves a temperature of between approximately −20° C. and approximately −25° C.

16. The system of claim 13, wherein independent manipulation of at least one of the third valve and the fourth valve delivers a mixture of refrigerant in the gaseous state and refrigerant in the liquid state to the treatment element of the cryoablation device.

17. The system of claim 13, wherein the refrigerant in the gaseous state is within a first portion of the refrigerant reservoir and the refrigerant in the liquid state is within a second portion of the refrigerant reservoir, the third valve being in fluid communication with the first portion and the fourth valve being in fluid communication with the second portion.

18. The system of claim 17, wherein the third and fourth valves are on opposite ends of the refrigerant reservoir.

* * * * *